United States Patent
Arnaud

(10) Patent No.: US 6,869,597 B2
(45) Date of Patent: Mar. 22, 2005

(54) COSMETIC CARE OR MAKEUP COMPOSITION FOR A KERATIN MATERIAL COMPRISING AT LEAST ONE PHOTOPROTECTIVE AGENT AND AT LEAST ONE ESTER COMPRISING AN AROMATIC GROUP

(75) Inventor: Pascal Arnaud, L'Hay les Roses (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 10/138,299

(22) Filed: May 6, 2002

(65) Prior Publication Data

US 2003/0077234 A1 Apr. 24, 2003

(30) Foreign Application Priority Data

May 4, 2001 (FR) ............................................. 01 06048

(51) Int. Cl.⁷ ............................. A61K 7/42; A61K 7/44; A61K 7/021; A61K 7/025; A61K 7/00
(52) U.S. Cl. .............................. 424/59; 424/60; 424/63; 424/64; 424/70.1; 424/400; 424/401
(58) Field of Search ............................... 424/59, 63, 64, 424/70.1, 400, 401; 554/220, 223, 227

(56) References Cited

U.S. PATENT DOCUMENTS

| | | | |
|---|---|---|---|
| 2,463,264 A | | 3/1949 | Graenacher et al. |
| 3,992,356 A | | 11/1976 | Jacquet et al. |
| 4,247,411 A | | 1/1981 | Vanlerberghe et al. |
| 5,008,101 A | | 4/1991 | Klimisch et al. |
| 5,166,355 A | | 11/1992 | Leistner et al. |
| 5,237,071 A | | 8/1993 | Leistner et al. |
| 5,585,091 A | | 12/1996 | Pelzer et al. |
| 5,762,947 A | | 6/1998 | Guerrero et al. |
| 5,932,197 A | * | 8/1999 | Arnaud .................. 424/64 |
| 5,955,060 A | | 9/1999 | Hüglin et al. |
| 5,959,130 A | | 9/1999 | Walele et al. |
| 5,962,452 A | | 10/1999 | Haase et al. |
| 5,976,512 A | | 11/1999 | Huber |

FOREIGN PATENT DOCUMENTS

| | | |
|---|---|---|
| DE | 197 26 184 | 12/1998 |
| EP | 0 517 104 | 12/1992 |
| EP | 0 570 838 | 11/1993 |
| EP | 0 669 323 | 8/1995 |
| EP | 0 775 698 | 5/1997 |
| EP | 0 796 851 | 9/1997 |
| EP | 0 848 944 | 6/1998 |
| EP | 0 863 145 | 9/1998 |
| EP | 0 878 469 | 11/1998 |
| EP | 0 893 119 | 1/1999 |
| EP | 0 933 376 | 8/1999 |
| EP | 0 989 111 | 3/2000 |
| FR | 2 315 991 | 1/1977 |
| FR | 2 416 008 | 8/1979 |
| FR | 1 097 699 A1 * | 9/2001 |
| GB | 2 206 339 | 1/1989 |
| GB | 2 303 549 | 2/1997 |
| WO | WO 93/04665 | 3/1993 |

OTHER PUBLICATIONS

English language Derwent Abstract of DE 197 26 184, Dec. 24, 1998.

English language Derwent Abstract of EP 0 989 111, Mar. 29, 2000.

English language Derwent Abstract of FR 2 315 991, Jan. 28, 1977.

* cited by examiner

Primary Examiner—Shelley A. Dodson
(74) Attorney, Agent, or Firm—Finnegan, Henderson, Farabow, Garrett & Dunner, L.L.P.

(57) ABSTRACT

A cosmetic care or makeup composition for keratin materials comprising, in a physiologically acceptable medium, at least one photoprotective agent capable of screening out UV radiation and at least one ester comprising an aromatic group, which is liquid at room temperature, resulting from the esterification of an aromatic acid with at least one hydroxyl group chosen from pendent hydroxyl group and terminal hydroxyl groups of hydroxylated aliphatic compounds said hydroxylated aliphatic compounds being chosen from hydroxylated aliphatic acids and esters thereof. Use of the said ester comprising an aromatic group to improve the photoprotective power of compositions intended for protecting the skin and/or the lips and/or integuments against UV radiation.

135 Claims, No Drawings

COSMETIC CARE OR MAKEUP COMPOSITION FOR A KERATIN MATERIAL COMPRISING AT LEAST ONE PHOTOPROTECTIVE AGENT AND AT LEAST ONE ESTER COMPRISING AN AROMATIC GROUP

The present invention relates to a cosmetic care or makeup composition intended especially for protecting human keratin materials such as the skin and/or the lips and/or integuments (nails, eyelashes, eyebrows, body hair or head hair) against ultraviolet radiation (UV). This composition in particular comprises a photoprotective agent that is capable of screening or blocking out UV radiation, and an ester comprising an aromatic group, which is liquid at room temperature, resulting from the esterification of an aromatic acid with at least one hydroxyl group chosen from pendent hydroxyl groups and terminal hydroxyl groups of hydroxylated aliphatic compounds chosen from hydroxylated aliphatic acids and esters thereof.

It is known that light radiation with wavelengths of between 280 nm and 400 nm permit tanning of the human epidermis and that light rays with wavelengths of between 280 and 320 nm, known as UV-B rays, cause skin burns and erythema that may be harmful to the development of a natural tan; this UV-B radiation should thus be screened out.

It is also known that UV-A rays, with wavelengths of between 320 and 400 nm, which cause tanning of the skin, are liable to induce an impairment in the skin, especially in the case of sensitive skin or of skin that is continually exposed to solar radiation. UV-A rays in particular cause a loss of elasticity of the skin and the appearance of wrinkles leading to premature ageing. They promote the triggering of the erythemal reaction or amplify this reaction in certain individuals and may even be the cause of phototoxic or photoallergic reactions. It is thus desirable also to screen out UV-A radiation.

Various types of antisun photoprotective agents commonly known as sunscreens, which are organic or inorganic, soluble or insoluble in the medium, and capable of absorbing or selectively blocking out harmful UV radiation, exist on the market to screen or block out UV-A and UV-B rays, these screening agents (and the amounts thereof) being selected as a function of the desired sun protection factor; this sun protection factor (SPF) is expressed mathematically as the ratio of the dose of UV radiation required to reach the erythema-forming threshold with the UV screening agent, to the dose of UV radiation required to reach the erythema-forming threshold without a UV screening agent.

The formulation of compositions containing sunscreens is the subject of considerable research with the aim of improving the efficacy of organic or inorganic (mineral) screening agents.

It is well known that the oils present in antisun compositions influence the absorption properties of the screening agents and the SPF values.

Formulators are thus in search of oils that have both very good properties of dissolving or dispersing organic and mineral screening agents, but also good sensory properties, in particular in terms of application.

The term "oil" means any non-aqueous compound that is liquid at room temperature (25° C.) and atmospheric pressure (760 mmHg).

According to the inventors, oils that have an aromatic radical in their chemical structure constitute a preferred family of solvents for organic screening agents since their structural similarity with these organic screening agents gives them very good solubilizing properties.

Mention may be made, for example, of $C_{12-15}$ alkyl benzoates (for instance Finsolv TN sold by the company Finetex), benzoic esters of branched alcohols, for instance those described in patent application EP-A-848 944 by C.P. Hall Company, or the phenylsilicones described in U.S. Pat. No. 5,008,101 from Dow Corning.

These solvents have sensory properties that are entirely suitable for preparing cosmetic products characterized on application by a dry, evanescent feel, and by the production of a relatively non-glossy film, for instance antisun products, care creams or lotions.

On the other hand, these solvents are not always suitable for formulating other products, in particular in the field of makeup, for instance lipsticks or cast foundations, or in the field of care, for instance lipcare balms or nourishing creams.

Aromatic esters obtained by reacting benzoic acid with hydroxylated acid esters, in particular castor oil, described in U.S. Pat. No. 5,959,130 from Finetex, are moreover known.

After extensive research conducted on these esters, the Inventor has found, surprisingly, that it is possible to substantially increase the photoprotective power of a composition intended for protecting against ultraviolet radiation, by combining in this composition a UV screening agent and a specific oil that is an ester comprising an aromatic group, which is liquid at room temperature, resulting from the esterification of an aromatic acid with at least one hydroxyl group chosen from pendent hydroxyl group and terminal hydroxyl groups of hydroxylated aliphatic compounds said hydroxylated aliphatic compounds being chosen from hydroxylated aliphatic acids and esters thereof.

One subject of the invention is thus a cosmetic care or makeup composition for a keratin material comprising, in a physiologically acceptable medium, at least one photoprotective agent capable of screening out UV radiation, a particulate phase and at least one ester comprising an aromatic group, which is liquid at room temperature, resulting from the esterification of an aromatic acid with at least one hydroxyl group chosen from pendent hydroxyl group and terminal hydroxyl groups of hydroxylated aliphatic compounds said hydroxylated aliphatic compounds being chosen from hydroxylated aliphatic acids and esters thereof.

The photoprotective agent, the particulate phase and the ester comprising an aromatic group in the composition according to the invention are separate compounds.

A subject of the present invention is also a cosmetic care or makeup composition for keratin materials comprising, in a physiologically acceptable medium, at least one photoprotective agent capable of screening out UV radiation, comprising one or more inorganic particulate screening agents and at least one ester comprising an aromatic group, which is liquid at room temperature, resulting from the esterification of an aromatic acid with at least one hydroxyl group chosen from pendent hydroxyl group and terminal hydroxyl groups of hydroxylated aliphatic compounds said hydroxylated aliphatic compounds being chosen from hydroxylated aliphatic acids and esters thereof.

Admittedly, it is described in U.S. Pat. No. 5,959,130 from Finetex that these esters containing an aromatic group have good pigment-dispersing properties and good properties in terms of solubilizing solid organic screening agents. However, the said document does not describe antisun compositions according to the present invention and it does not mention or suggest the ability of these esters to significantly increase the SPF of such compositions.

The composition according to the present invention can be in the form of a composition intended for protecting the skin and/or the lips and/or integuments against UV radiation such as solar radiation.

Another subject of the invention is the use of at least one ester containing an aromatic group, which is liquid at room temperature, resulting from the esterification of an aromatic acid with at least one hydroxyl group chosen from pendent hydroxyl group and terminal hydroxyl groups of hydroxylated aliphatic compounds said hydroxylated aliphatic compounds being chosen from hydroxylated aliphatic acids and esters thereof, in a cosmetic composition or for the manufacture of a physiological composition intended for protecting the skin and/or the lips and/or integuments against UV radiation, containing at least one photoprotective agent, to improve the photoprotective power of the said composition.

The expression "physiological composition" means a non-toxic cosmetic or dermatological composition that can be applied to the skin, integuments and/or the lips of the face of human beings.

A subject of the invention is also the use of at least one ester comprising an aromatic group, which is liquid at room temperature, resulting from the esterification of an aromatic acid with at least one hydroxyl group chosen from pendent hydroxyl group and terminal hydroxyl groups of hydroxylated aliphatic compounds said hydroxylated aliphatic compounds being chosen from hydroxylated aliphatic acids and esters thereof, in an antisun cosmetic composition or for the manufacture of an antisun physiological composition containing at least one photoprotective agent.

Another subject of the invention is a cosmetic process for protecting the skin, the lips and/or integuments of human beings against solar radiation, which comprises introducing, into a cosmetic composition containing at least one photoprotective agent, an effective amount of an ester comprising an aromatic group, which is liquid at room temperature, resulting from the esterification of an aromatic acid with at least one hydroxyl group chosen from pendent hydroxyl group and terminal hydroxyl groups of hydroxylated aliphatic compounds said hydroxylated aliphatic compounds being chosen from hydroxylated aliphatic acids and esters thereof.

A subject of the invention is also a process for increasing the antisun protective properties of a cosmetic composition comprising at least one photoprotective agent, which comprises introducing into the said composition an effective amount of an ester comprising an aromatic group, which is liquid at room temperature, resulting from the esterification of an aromatic acid with at least one hydroxyl group chosen from pendent hydroxyl group and terminal hydroxyl groups of hydroxylated aliphatic compounds said hydroxylated aliphatic compounds being chosen from hydroxylated aliphatic acids and esters thereof.

Finally, a subject of the invention is a process for increasing the sun protection factor of a cosmetic composition comprising at least one photoprotective agent, which comprises introducing into the said composition an effective amount of an ester comprising an aromatic group, which is liquid at room temperature, resulting from the esterification of an aromatic acid with at least one hydroxyl group chosen from pendent hydroxyl group and terminal hydroxyl groups of hydroxylated aliphatic compounds said hydroxylated aliphatic compounds being chosen from hydroxylated aliphatic acids and esters thereof.

In addition to increasing the protection factor, the ester containing an aromatic group according to the invention gives the composition good sensory properties in terms of spreading and slipperiness and also gives the deposited film properties of good staying power over time and absence of stickiness and greasiness. The composition obtained also shows good homogeneity and good thermal stability (no demixing of the composition). Obtaining a deposit with good homogeneity is particularly desired for a makeup product.

For the purposes of the present invention, the expression "photoprotective agent" means any compound or any combination of compounds that, by mechanisms of absorption and/or reflection and/or scattering of UV-A and/or UV-B radiation, makes it possible to prevent, or at least to limit, contact between the said radiation and the surface of the skin, the lips and/or integuments onto which this or these compound(s) has (have) been applied.

These compounds may be hydrophilic organic screening agents and/or lipophilic organic screening agents that are active in the UV-A and/or UV-B range and/or inorganic screening agents such as UV-scattering and/or UV-reflecting mineral pigments or nanopigments, and also mixtures thereof.

The photoprotective agent can, for example, represent from 0.1% to 45% such as from about 0.5% to about 25% of the total weight of the composition.

For example, the photoprotective agent can contain one or more particulate screening agents, namely one or more screening agents that are insoluble at room temperature in the physiologically acceptable medium of the composition. For example, these particulate screening agents are inorganic or mineral screening agents.

For example, the inorganic particulate screening agent(s) can be chosen from treated or untreated metal oxide pigments or nanopigments, capable of physically blocking out the UV radiation, by scattering and/or reflection.

The expression "treated pigments or nanopigments" means pigments that have undergone one or more surface treatments of chemical, electronic, mechanochemical and/or mechanical nature with compounds as described, for example, in Cosmetics & Toiletries, February 1990, Vol. 105, pp. 53–64, such as amino acids, beeswax, fatty acids, fatty alcohols, anionic surfactants, lecithins, sodium, potassium, zinc, iron or aluminium salts of fatty acids, metal alkoxides (of titanium or aluminium), polyethylene, silicones, proteins (collagen, elastin), alkanolamines, fluoro compounds, silicon oxides, metal oxides, sodium hexametaphosphate, alumina or glycerol.

According to an embodiment of the invention, the inorganic particulate screening agents can be chosen from treated or untreated nanopigments of titanium oxide (amorphous or crystallized in rutile and/or anatase form), zinc oxide, iron oxide, zirconium oxide or cerium oxide, and mixtures thereof.

The treated nanopigments can be nanotitanium oxides treated with:
  silica and alumina, such as the products "Microtitanium Dioxide MT 500 SA" and "Microtitanium Dioxide MT 100 SA" from the company Tayca, and the products "Tioveil Fin", "Tioveil OP", "Tioveil MOTG" and "Tioveil IPM" from the company Tioxide,
  alumina and aluminium stearate, such as the product "Microtitanium Dioxide MT 100 T" from the company Tayca,
  alumina and aluminium laurate, such as the product "Microtitanium Dioxide MT 100 S" from the company Tayca,
  iron oxides and iron stearate, such as the product "Microtitanium Dioxide MT 100 F" from the company Tayca,
  silica, alumina and silicone, such as the products "Microtitanium Dioxide MT 100 SAS", "Microtitanium Dioxide MT 600 SAS" and "Microtitanium Dioxide MT 500 SAS" from the company Tayca, sodium hexametaphosphate, such as the product "Microtitanium Dioxide MT 150 W" from the company Tayca, octyltrimethoxysilane, such as the product "T-805" from the company Degussa, alumina and stearic acid, such as the product "UVT-M160" from the company Kemira, alumina and glycerol, such as the product "UVT-M212" from the company Kemira, alumina and silicone, such as the product "UVT-M262" from the company Kemira.

The untreated nanotitanium oxides may be, for example, those sold by the company Tayca under the trade names "Microtitanium Dioxide MT 500 B" or "Microtitanium Dioxide MT 600 B".

The untreated nanozinc oxides may be, for example, those sold by the company Sumitomo under the name "Ultra Fine Zinc Oxide Powder", by the company Presperse under the name "Finex 25", by the company Ikeda under the name "MZO-25" or by the company Sunsmart under the name "Z-Cote". The treated nanozinc oxides may be, for example, those sold by the company Sunsmart under the name "Z-Cote HP 1".

The nanopigments may be introduced into the compositions according to the invention in unmodified form or in the form of a pigmentary paste, that is to say as a mixture with a dispersant, as described, for example, in document GB-A-2 206 339.

For example, nanopigments containing elementary particles ranging from 5 to 500 nm, such as from 10 to 250 nm, and further such as from 10 to 100 nm, for example from 10 to 50 nm in size, can be chosen.

The nanopigments may, for example, represent from 0.1% to 30% such as from 0.5% to 15% of the total weight of the composition according to the invention.

The hydrophilic or lipophilic UV-A-active and/or UV-B-active organic screening agents may be chosen from cinnamic derivatives; dibenzoylmethane derivatives; salicylic derivatives (lipophilic screening agents), camphor derivatives; triazine derivatives (lipophilic screening agents) such as those described in patent applications U.S. Pat. No. 4,367,390, EP 863 145, EP 517 104, EP 570 838, EP 796 851, EP 775 698, EP 878 469 and EP 933 376; benzophenone derivatives; β,β'-diphenylacrylate derivatives, benzimidazole derivatives; bis-benzazolyl derivatives such as those described in patents EP-A 0 669 323 and U.S. Pat. No. 2,463,264; bis-hydroxyphenolbenzotriazole derivatives such as those described in patent applications U.S. Pat. No. 5,237,071, U.S. Pat. No. 5,166,355, GB-A-2 303 549, DE 197 26 184 and EP-A-893 119; p-aminobenzoic acid derivatives (hydrophilic screening agents); hydrocarbon-based screening polymers, lipophilic screening silicones such as those described in patent application WO-93/04665, and mixtures thereof.

Examples of UV-A-active and/or UV-B-active lipophilic organic screening agents that may be mentioned include:
p-aminobenzoic acid,
oxyethylenated (25 mol) p-aminobenzoate,
2-ethylhexyl p-dimethylaminobenzoate,
N-oxypropylenated ethyl p-aminobenzoate,
glyceryl p-aminobenzoate,
homomenthyl salicylate,
2-ethylhexyl salicylate,
triethanolamine salicylate,
4-isopropylbenzyl salicylate,
4-tert-butyl-4'-methoxydibenzoylmethane,
4-isopropyldibenzoylmethane,
2-ethylhexyl 4-methoxycinnamate,
methyl diisopropylcinnamate,
isoamyl 4-methoxycinnamate,
diethanolamine 4-methoxycinnamate,
menthyl anthranilate,
2-ethylhexyl 2-cyano-3,3'-diphenylacrylate,
ethyl 2-cyano-3,3'-diphenylacrylate,
2-hydroxy-4-methoxybenzophenone,
2,4-dihydroxybenzophenone,
2,2',4,4'-tetrahydroxybenzophenone,
2,2'-dihydroxy-4,4'-dimethoxybenzophenone,
2-hydroxy-4-n-octoxybenzophenone,
2-hydroxy-4-methoxy-4'-methylbenzophenone,
3-(4'-methylbenzylidene)-d,l-camphor,
3-benzylidene-d,l-camphor,
urocanic acid,
2,4,6-tris[p-(2'-ethylhexyl-1'-oxycarbonyl)anilino]-1,3,5-triazine,
2-[p-(tert-butylamido)anilino]-4,6-bis[(p-(2'-ethylhexyl-1'-oxycarbonyl)anilino]-1,3,5-triazine,
2,4-bis{[4-(2-ethylhexyloxy)]-2-hydroxyphenyl}-6-(4-methoxyphenyl)-1,3,5-triazine;
the polymer of N-(2 and 4)-[(2-oxoborn-3-ylidene)methyl]benzyl]acrylamide,
polyorganosiloxanes containing a benzalmalonate function,
polyorganosiloxanes containing a benzotriazole function, such as drometrizole trisiloxane, and mixtures thereof.

As UV-A-active and/or UV-B-active hydrophilic organic screening agents that may be used in the present invention, mention may be made of:
2-phenylbenzimidazole-5-sulphonic acid and its salts,
α-(2-oxoborn-3-ylidene)tolyl-4-sulphonic acid and its soluble salts,
2-hydroxy-4-methoxybenzophenone-5-sulphonate,
3-(4'-trimethylammonium)benzylidenebornan-2-one methyl sulphate,
3-(4'-sulpho)benzylidenebornan-2-one and its soluble salts,
1,4-bis(benzimidazolyl)phenylene-3,3',5,5'-tetrasulphonic acid and its soluble salts,
benzene-1,4-bis(3-methylidene-10-camphorsulphonic acid) and its soluble salts.

As organic screening agents that are insoluble in the medium, mention may be made of 2,2'-methylenebis[6-(2H-benzotriazol-2-yl)-4-(1,1,3,3-tetramethylbutyl)phenol] or the compound (2,2'-methylenebis[6-(2H-benzotriazol-2-yl)-4-(methyl)phenol].

As organic lipophilic screening agents that can be used in the present invention, mention may be made of:
  4-tert-butyl-4'-methoxydibenzoylmethane sold under the trade name "Parsol 1789" by the company Hoffmann LaRoche;
  octyl methoxycinnamate sold under the trade name "Parsol MCX" by the company Hoffmann LaRoche
  2-ethylhexyl α-cyano-β,β-diphenylacrylate (octocrylene) sold under the trade name "Uvinul N 539" by the company BASF;
  4-methylbenzylidenecamphor sold under the trade name "Eusolex 6300" by Merck;
  benzophenone-3 (oxybenzone) sold under the trade name "Uvinul M40" by BASF;
  2-ethylhexyl salicylate or octyl salicylate, sold under the trade name Neo Heliopan OS by Haarmaan & Reimer;
  2,4,6-tris[p-(2'-ethylhexyl-1'-oxycarbonyl)anilino]-1,3,5-triazine sold under the trade name "Uvinul T 150" by the company BASF;

drometrizole trisiloxane sold under the trade name "Silatrizole" by the company Rhodia Chimie.

As hydrophilic organic screening agents that can be used in the present invention, mention may be made of benzene-1,4-bis(3-methylidene-10-camphorsulphonic acid) sold under the trade name "Mexoryl SX" by Chimex, and 2-phenylbenzimidazole-5-sulphonic acid sold under the trade name "Eusolex 232" by the company Merck; and mixtures thereof.

One or more organic screening agents that are soluble in the physiologically acceptable medium of the composition according to the invention may be chosen.

The organic screening agents may, for example, represent from 0.1% to 15% such as from 1% to 10% of the total weight of the composition according to the invention.

The composition according to the invention can also contain one or more esters comprising an aromatic group, which is (are) liquid at room temperature, resulting from the esterification of an aromatic acid with at least one hydroxyl group chosen from pendent hydroxyl group and terminal hydroxyl groups of hydroxylated aliphatic compounds said hydroxylated aliphatic compounds being chosen from hydroxylated aliphatic acids and esters thereof.

The expression "hydroxylated aliphatic compound" means an aliphatic hydroxycarboxylic acid or an aliphatic hydroxycarboxylic acid ester. The acid (non-esterified) may contain from 2 to 40 carbon atoms, such as from 10 to 34 carbon atoms and further such as from 12 to 28 carbon atoms; it also may comprise from 1 to 20 hydroxyl groups, such as from 1 to 10 hydroxyl groups and further such as from 1 to 6 hydroxyl groups, which may be esterified with the aromatic acid. The hydroxylated compound in ester form results from the esterification of the —COOH function of an aliphatic hydroxycarboxylic acid with an aliphatic alcohol that may contain from 1 to 40 carbon atoms, such as from 3 to 30 carbon atoms. This alcohol may be a monoalcohol or a polyol. The esters derived from the reaction of the aliphatic hydroxycarboxylic acid with a polyol may be partially or totally esterified esters.

For example, the hydroxylated aliphatic compound can be chosen from esters derived from aliphatic hydroxycarboxylic acid. In other words, the liquid ester containing an aromatic group of the composition of the invention is an ester of an ester. For example, this ester containing an aromatic group is an ester of a fatty acid ester whose fatty acid residue contains at least 12 carbon atoms. For example, the hydroxyl group involved in the esterification with the aromatic acid is borne on the acid portion of the hydroxylated compound.

According to the invention, the composition may contain one or more esters containing an aromatic group, which are liquid at room temperature (25° C.) and atmospheric pressure (760 mmHg).

When the hydroxyl group of the hydroxylated aliphatic compound involved in the esterification with the aromatic acid is at the end of a chain, this group is in an α-ω position relative to the —COOH function of the aliphatic hydroxycarboxylic acid.

The aromatic acid may be chosen from the following carboxylic acids:
a) monoacids, such as benzoic acid, phenylacetic acid, cinnamic acid, 3-phenylpropanoic acid or salicylic acid;
b) diacids such as terephthalic acid;
c) triacids such as trimellitic acid;
d) tetra-acids such as pyromellitic acid;
and mixtures thereof.

For example, the aromatic acid is not hydroxylated (in particular, the aromatic group is not hydroxylated).

For example, the aromatic carboxylic acid can be benzoic acid.

As esters that may be used in the invention, mention may be made of those resulting from the esterification of at least one aromatic acid with at least one of the following aliphatic hydroxylated carboxylic acids:
i) saturated linear monohydroxylated aliphatic monoacids of formula:

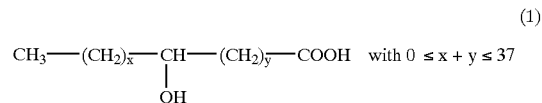

for instance lactic acid (x+y=0); 12-hydroxyoctadecanoic acid (or 12-hydroxystearic acid) of formula:

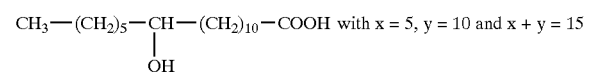

and α-hydroxyoctadecanoic acid

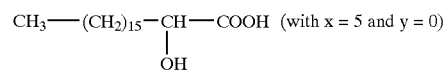

or (2) HO—CH$_2$—(CH$_2$)$_x$—COOH with $0 \leq x \leq 38$
for instance glycolic acid HO—CH$_2$—COOH (x=0); or juniperic acid (16-hydroxyhexadecanoic acid) of formula HO—CH$_2$—(CH$_2$)$_{14}$—COOH with x=14;
ii) saturated branched monohydroxylated aliphatic monoacids of formula:

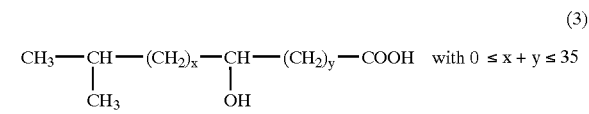

for instance 5-methyl-2-hydroxyhexanoic acid (leucinic acid) of formula:

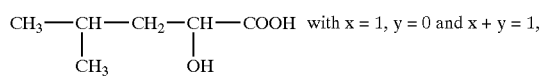

or (3') alternatively 2-ethyl-3-hydroxycaprylic acid of formula:

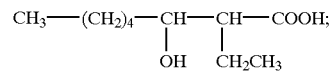

iii) unsaturated monohydroxylated aliphatic monoacids of formula:

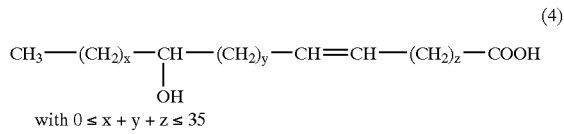

for instance 12-hydroxy(cis)-9-octadecenoic acid (or ricinoleic acid) of formula:

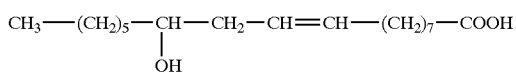

with x = 5, y = 1, z = 7 and x + y + z = 13 or

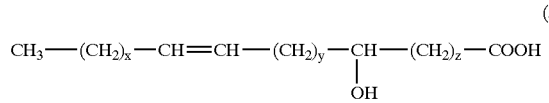

(5)

with 0 ≤ x + y + z ≤ 35 for instance 3-hydroxy-4-hexanoic acid of formula:

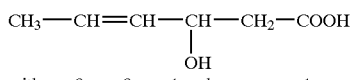

with x = 0, y = 0, z = 1 and x + y + z = 1 or 2-hydroxy-15-tetracosenoic acid (or oxynervonic acid) of formula:

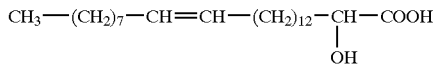

with x = 7, y = 12, z = 0 and x + y + z = 17 or (6) $HOCH_2-(CH_2)_x-CH=CH-(CH_2)_y-COOH$ with $0 \leq x+y \leq 36$ for instance 16-hydroxy-6-hexadecenoic acid with x=8, y=4 and x+y=12 of formula $HO-CH_2-(CH_2)_8-CH=CH-(CH_2)_4-COOH$;

iv) saturated polyhydroxylated aliphatic monoacids of formula:

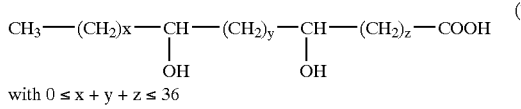

(7)

with 0 ≤ x + y + z ≤ 36 for instance 9,10-dihydroxyoctadecanoic acid of formula:

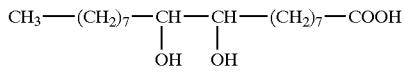

with x = 7, y = 0, z = 7 and x + y + z = 14 for instance 9,12-dihydroxyoctadecanoic acid of formula: 7 with x=5, y=2, z=7 and x+y+z=14 or 9,10,16-trihydroxyhexadecanoic acid (aleuritic acid) or 9,10,12-trihydroxyoctadecanoic acid of formula:

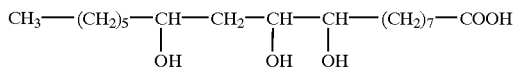

or hexahydroxyoctadecanoic acid and octahydroxyoctadecanoic acid;

v) saturated monohydroxylated aliphatic polyacids of formula:

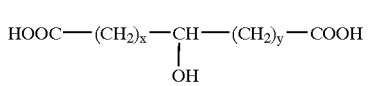

(8)

with 0 ≤ x + y ≤ 37, for instance malic acid, or citric acid; and vi) saturated polyhydroxylated aliphatic polyacids, for instance tartaric acid;

and mixtures thereof.

As other aliphatic hydroxylated compounds that may be used in the invention, mention may be made of those resulting from the esterification of at least one aromatic acid with at least one of the following aliphatic hydroxylated acid esters:

vii) saturated linear monohydroxylated aliphatic monoacid esters such as:

lactic acid esters, for instance isostearyl lactate, the lactate derived from $C_{12}-C_{13}$ alcohol, octyldodecyl lactate, oleyl lactate or myristyl lactate;

12-hydroxyoctadecanoic (or 12-hydroxystearic) acid esters, for instance 2-ethylhexyl hydroxystearate, octyldodecyl hydroxystearate, isostearyl hydroxystearate, isodecyl hydroxystearate, glyceryl trihydroxystearate (or hydrogenated castor oil) or dipentaerythrityl hexahydroxystearate;

viii) unsaturated monohydroxylated aliphatic monoacid esters such as ricinoleic acid (or 12-hydroxy(cis)-9-octadecenoic acid) esters, for instance butyl ricinoleate, octyldodecyl ricinoleate, cetyl ricinoleate, glyceryl triricinoleate or castor oil;

ix) saturated monohydroxylated aliphatic polyacid esters such as diisostearyl malate, triisostearyl citrate or trioctyldodecyl citrate;

x) saturated polyhydroxylated aliphatic polyacid esters, for instance the tartrate derived from the reaction with 2 branched $C_{12}-C_{13}$ alcohols;

and mixtures thereof.

As hydroxylated compounds in ester form that may be used in the invention and that result from the esterification of a polyol, mention may be made in general of:

xi) partial or total esters of a $C_2$ to $C_{16}$ polyol that is reacted with a hydroxylated aliphatic acid, such as, especially, triglycerides, pentaerythritol esters, neopentyl glycol esters, dipentaerythritol esters, polyglycerol esters or sorbitol esters;

and mixtures thereof.

For instance, the esters containing an aromatic group of the invention are chosen from esters of an aliphatic fatty acid ester in which the fatty acid residue contains at least 12 carbon atoms. For example, the hydroxylated compound is chosen from ricinoleic acid esters, 12-hydroxystearic acid esters, lactic acid esters and 14-hydroxyeicosenoic acid esters, and mixtures thereof.

Esters containing an aromatic group that can be used include:

the ester resulting from the esterification reaction of castor oil with benzoic acid in proportions of 1 to 1 (1/1), for example sold by the company Finetex under the name Finsolv BCO-110, which will be referred to hereinbelow as glyceryl monobenzoyl ricinoleate, the compound resulting from the reaction of castor oil with benzoic acid in proportions of 1 to 1.5 (1/1.5), for example sold by the company Finetex under the reference Finsolv BCO-115, which will be referred to hereinbelow as glyceryl mono-dibenzoyl ricinoleate, the compound resulting from the esterification reaction of castor oil with benzoic acid in proportions of 1 to 2 (1/2), for example sold by the company Finetex under the reference Finsolv BCO-120, which will be referred to hereinbelow as glyceryl dibenzoyl ricinoleate, the compound resulting from the esterification reaction of castor oil with benzoic acid in proportions of 1 to 3 (1/3), for example sold by the company Finetex under the reference Finsolv BCO-130, which will be referred to hereinbelow as glyceryl tribenzoyl ricinoleate, and mixtures thereof.

For example, the ester containing an aromatic group can be glyceryl mono-dibenzoyl ricinoleate.

For example, the ricinoleic acid represents from 80% to 92% of the castor oil. Thus, its esterification leads predominantly (80% to 92%) to the ester of the ricinoleic acid ester.

The ester resulting from the esterification reaction with benzoic acid of lesquerella oil predominantly containing (52% to 57%) an ester of 14-hydroxyeicosenoic acid, or lesquerolic acid, may also be used.

The ester containing an aromatic group of the composition of the invention may be manufactured according to the process described in document U.S. Pat. No. 5,959,130; the disclosure of which is incorporated herein.

The ester containing an aromatic group of the composition of the invention may represent from 0.1% to 99.9% of the total weight of the composition, such as from 1% to 99% and further such as from 5% to 90%, for example from 5% to 70%.

For example, the ester containing an aromatic group/photoprotective agent ratio in the compositions according to the invention may range, such as from 999:1 to 0.01:1 and further such as from 200:1 to 1:1.

According to an embodiment, the composition according to the invention comprises a particulate phase. The expression "particulate phase" means a phase containing one or more particles that are solid at room temperature, amorphous or crystalline, and insoluble in the medium at room temperature and even above the melting point or softening point of said medium.

This particulate phase may be present in a proportion of from 0.01% to 40% of the total weight of the composition, such as from 0.5% to 25%.

It may comprise pigments and/or nacres and/or fillers usually used in cosmetic compositions. The pigments may be white or coloured, mineral or organic, coated or uncoated, and of standard or nanometric size; they are insoluble in the physiologically acceptable medium of the composition according to the invention. They are intended to colour and/or opacify the composition. These pigments may be inorganic (or mineral) particulate screening agents such as the UV-scattering and/or UV-reflecting mineral pigments or nanopigments mentioned above. Among the mineral pigments that may be mentioned are titanium dioxide, zinc dioxide, zirconium dioxide or cerium dioxide, and also zinc oxide, iron oxide, chromium oxide, ferric blue, chromium hydrate, ultramarines (aluminosilicate polysulphides), manganese pyrophosphate and certain metal powders such as silver or aluminium powder. Among the organic pigments that may be mentioned are carbon black and lakes based on cochineal carmine or on barium, strontium, calcium or aluminium. The pigments may be present in the composition in a proportion of from 0.05% to 40% of the total weight of the composition, such as in a proportion of from 2% to 20%.

The particulate phase may also comprise organic screening agents that are insoluble in the medium, such as the screening agents mentioned above.

The terms "nacres" and "nacreous pigments" should be understood as meaning iridescent particles, especially produced by certain molluscs in their shell or else synthesized, which are insoluble in the physiologically acceptable medium of the composition.

The nacres may be present in the composition in a proportion of from 0.01% to 20% by weight, such as from 1% to 15% by weight, and may be chosen from white nacreous pigments such as mica coated with titanium or with bismuth oxychloride, coloured nacreous pigments such as titanium mica with iron oxides, titanium mica with, ferric blue or chromium oxide, or titanium mica with an organic pigment of the above mentioned type.

For example, the composition according to the invention can contain pigments and/or nacres, these compounds may differ from the photoprotective agent(s) present in the said composition.

The fillers may be chosen from talc, mica, silica, kaolin, polyamide powder, poly-β-alanine powder, polyethylene powder, tetrafluoroethylene polymer powders, lauroyllysine, starch, boron nitride, hollow polymer microspheres, acrylic polymer particles, silicone resin microbeads, precipitated calcium carbonate, dicalcium phosphate, magnesium carbonate, magnesium hydrocarbonate, hydroxyapatite, hollow silica microspheres, glass or ceramic microcapsules, metal soaps derived from organic carboxylic acids containing from 8 to 22 carbon atoms, such as from 12 to 18 carbon atoms, and mixtures thereof. The fillers may be present in a proportion of from 0.01% to 35% by weight, such as from 0.5% to 15% in the composition.

The composition may also contain an aqueous phase comprising water and optionally one or more compounds that are fully or partially soluble in water.

The composition of the invention may comprise, in addition to the ester containing an aromatic group, at least one additional fatty substance chosen from waxes, fatty substances that are liquid at room temperature (25° C.) and atmospheric pressure (760 mmHg) other than the said ester containing an aromatic group, also known as oils, fatty substances that are pasty at room temperature, gums, resins and lipophilic polymers, and mixtures thereof.

These additional fatty substances can represent from 0.01% to 90% of the total weight of the composition, such as from 0.05% to 60%, and further such as from 1% to 35%.

The oils may be hydrocarbon-based oils and/or silicone oils and/or fluoro oils. These oils may be of animal, plant, mineral or synthetic origin. The expression "hydrocarbon-based oil" means an oil mainly comprising carbon and hydrogen atoms and possibly one or more functions chosen from hydroxyl, ester, ether and carboxylic functions. As examples of oils that may be used in the invention, mention may be made of:

hydrocarbon-based oils of animal origin, such as perhydrosqualene;

hydrocarbon-based oils of plant origin, such as liquid triglycerides of fatty acids containing from 4 to 24 carbon atoms, for instance heptanoic or octanoic acid triglycerides or alternatively, sunflower oil, corn oil, soybean oil, marrow oil, grapeseed oil, sesame oil, hazelnut oil, apricot oil, macadamia oil, castor oil, avocado oil, caprylic/capric acid triglycerides for instance those sold by the company Stearineries Dubois or those sold under the names Miglyol 810, 812 and 818 by the company Dynamit Nobel, jojoba oil or karite butter oil;

linear or branched hydrocarbons of mineral or synthetic origin, such as liquid paraffins, and derivatives thereof, petroleum jelly, polydecenes, and hydrogenated polyisobutene such as Parleam;

synthetic esters and synthetic ethers, especially of fatty acids, for instance oils of formula $R_1COOR_2$ in which $R_1$ represents an upper fatty acid residue containing from 1 to 40 carbon atoms and $R_2$ represents a hydrocarbon-based chain containing from 1 to 40 carbon atoms with $R_1+R_2 \geq 10$, such as, for example, purcellin oil, isononyl isononanoate, isopropyl myristate, 2-ethylhexyl palmitate, 2-octyldodecyl stearate, 2-octyldodecyl erucate isostearyl isostearate or tridecyl trimellitate; hydroxylated esters such as isostearyl lactate, octyl hydroxystearate, octyldodecyl hydroxystearate, diisostearyl malate, triisocetyl citrate and fatty alkyl heptanoates, octanoates and decanoates; polyol esters, for instance propylene glycol dioctanoate, neopentyl glycol diheptanoate and diethylene glycol diisononanoate; and pentaerythritol esters, for instance pentaerythrityl tetraisostearate;

fatty alcohols containing from 12 to 26 carbon atoms, for instance, octyldodecanol, 2-butyloctanol, 2-hexyldecanol, 2-undecylpentadecanol, oleyl alcohol;

fluoro oils that may be partially hydrocarbon-based and/or silicone-based;

silicone oils, for instance linear or cyclic volatile or non-volatile polydimethylsiloxanes (PDMSs); polydimethylsiloxanes comprising alkyl, alkoxy or phenyl groups, that are pendent or at the end of a silicone chain, these groups containing from 2 to 24 carbon atoms; phenylsilicones, for instance phenyltrimethicones, phenyldimethicones, phenyltrimethylsiloxydiphenylsiloxanes, diphenyldimethicones, diphenylmethyldiphenyltrisiloxanes, 2-phenylethyltrimethylsiloxysilicates;

mixtures thereof.

For example, the composition according to the invention comprises a wax. The term "wax" means a crystalline compound that is soluble in the medium above its melting point and insoluble in the medium at room temperature.

As waxes that may be used in the invention, mention may be made of those generally used in cosmetics: they are especially of natural origin, optionally modified, for instance lanolin, oxypropylenated or acetylated lanolin, beeswax, carnauba wax, candelilla wax, ouricoury wax, Japan wax, cork fibre wax, sugarcane wax, rice wax, montan wax, paraffin, lignite wax, microcrystalline wax, ceresin, ozokerite, hydrogenated oils, for instance hydrogenated jojoba oil or hydrogenated castor oil; synthetic waxes, for instance polyethylene waxes derived from the polymerization or copolymerization of ethylene and Fischer-Tropsch waxes, or alternatively fatty acid esters, for instance octacosanyl stearate, glycerides that are solid at 30° C. or at 45° C., silicone waxes, for instance alkyldimethicones or alkoxydimethicones containing an alkyl or alkoxy chain of 10 to 45 carbon atoms, poly(di)methylsiloxane esters that are solid at 30° C., the ester chain of which contains at least 10 carbon atoms; and mixtures thereof.

The composition according to the invention may also comprise one or more additives usually used in the field under consideration, such as softeners, antioxidants, preserving agents, opacifiers, neutralizers, stabilizers, emollients, silicones, fluoro compounds, antifoams, fragrances, surfactants, polymers, propellants, acidifying or basifying agents, lipophilic gelling agents or liquid fatty substances, aqueous-phase gelling agents, dispersants, dyestuffs and cosmetic active agents. These additives may be present in the composition in a proportion of from 0.001% to 30% of the total weight of the composition, such as from 0.005% to 15%.

Dyestuffs that may be mentioned include water-soluble or liposoluble dyes, especially natural organic dyes such as cochineal carmine, and/or synthetic dyes such as halo acid dyes, azo dyes and anthraquinone dyes. Mention may also be made of mineral dyes such as copper sulphate.

Among the cosmetic active agents that may be present in the composition, mention may be made of α-hydroxy acids, insect repellents, anti-inflammatories, substance P antagonists, vitamins A, E, C and $B_3$, provitamins, for instance D-panthenol, calmants, for example α-bisabolol, aloe vera, allantoin, plant extracts or essential oils, protective agents or restructuring agents, for instance ceramides, refreshing active agents, for instance menthol and its derivatives, emollients (cocoa butter, dimethicone), moisturizers (arginine PCA), glycerol, antiwrinkle active agents and essential fatty acids, and mixtures thereof.

The compositions according to the invention may also contain agents for artificially tanning and/or browning the skin (self-tanning agents), such as, for example, dihydroxyacetone (DHA).

Needless to say, a person skilled in the art will take care to select the nature and concentration of these adjuvants such that they do not reduce the protection factor of the composition and do not destabilize the said composition.

The compositions according to the invention may be in the form of an oily solution, an oily or anhydrous gel, an oil-in-water or water-in-oil emulsion, a multiple emulsion, or a dispersion of oil in water by means of vesicles.

When it is an emulsion, the aqueous phase of this emulsion may comprise a nonionic vesicular dispersion prepared according to known processes (Bangham, Standish and Watkins. J. Mol. Biol. 13, 238 (1965), FR 2 315 991 and FR 2 416 008).

In an embodiment of the invention, the composition according to the invention may be prepared in the usual manner by a person skilled in the art. It may be in the form of a cast product, and for example in the form of a stick or tube, in the form of a soft paste or alternatively a gel, a more or less fluid cream, a milk, an ointment, a powder, an aerosol mousse or a spray.

For example, the composition according to the invention can be in the form of a more or less rigid stick.

The cosmetic composition of the invention may be used as a composition for protecting the human epidermis or the hair against ultraviolet rays, as an antisun composition or as a makeup product.

In the instance when the cosmetic composition according to the invention is used for protecting the human epidermis against UV rays, or as an antisun composition, it may be in the form of a cast product, a soft paste, a cream, a milk, an ointment, a gel, a cream gel, a stick or a solid tube, a powder, an aerosol foam or a spray.

In the instance when the cosmetic composition according to the invention is used for protecting the hair against UV rays, it may be in the form of a shampoo, a conditioner, for use before or after dyeing or bleaching, or before, during or after permanent waving or straightening the hair, a styling or treating lotion or gel, a blow-drying or hairsetting lotion or gel, or a composition for permanent-waving, straightening, dyeing or bleaching the hair.

The composition may be used as a makeup composition for the eyelashes, the eyebrows, the skin or the lips, such as an epidermal treatment cream, a foundation, a tube of lipstick, a lip gloss, a product with care properties such as a lip balm, an eyeshadow, a face powder, a mascara, an eyeliner or a skin colouring product (such as a self-tanning product).

For example, the composition according to the invention is a makeup composition for the lips.

According to an embodiment, the composition is in anhydrous form (less than 5% water).

For example, the composition is in solid form at room temperature.

The examples that follow are intended to illustrate the present invention in a non-limiting manner.

The amounts are given as percentages by mass.

EXAMPLES 1 TO 5

Influence of the Esters According to the Invention on the SPF in the Presence of Nanotitanium Oxide The inventors compared the influence of the esters containing an aromatic group according to the invention on the SPF with castor oil and 2-octyldodecyl neopentanoate, the photoprotective agent being a nanotitanium oxide.

Compositions 1, 2, 3, 4 and 5 below are prepared:

| | | Composition (%) | | | | |
|---|---|---|---|---|---|---|
| | Phase | Ex. 1 (comparative) | Ex. 2 (comparative) | Ex. 3 (invention) | Ex. 4 (invention) | Ex. 5 (invention) |
| Castor oil | A | 88 | | | | |
| 2-Octyldodecyl neopentanoate | | | 88 | | | |
| Glyceryl dibenzoyl ricinoleate | | | | 88 | | |
| Glyceryl tribenzoyl ricinoleate | | | | | 88 | |
| Glyceryl mono-dibenzoyl ricinoleate | | | | | | 88 |
| Nanotitanium oxide (UV-Titan M 262 sold by the company Kemira) | B | 3 | 3 | 3 | 3 | 3 |
| Octacosanyl stearate | C | 9 | 9 | 9 | 9 | 9 |
| | | 100 | 100 | 100 | 100 | 100 |

Procedure

The titanium oxide (phase B) is ground in a portion of the oily phase A.

The wax (phase C) is added along with the remaining portion of phase A into the ground material obtained above.

The mixture is homogenized at 100° C. by stirring with a magnetic bar.

The mixture is cast at 100° C. into a mould at 41–42° C.

Measurement of the SPF in vitro

The sun protection factor (SPF) was determined for each of Examples 1 to 5 according to the "in vitro" method described by B. L. Diffey in J. Soc. Cosmet. Chem. 40, 127–133, (1989).

The measurements were performed using a UV-visible SPF 290S spectrophotometer from Optometrics equipped with an integration sphere and a xenon lamp, at room temperature.

Each composition is applied to a Transpore adhesive tape from 3M, stuck to a quartz slide, in the form of a homogeneous and uniform deposit in a proportion of 1.5 mg/cm$^2$.

Results

| | Examples | | | | |
|---|---|---|---|---|---|
| | No. 1 | No. 2 | No. 3 | No. 4 | No. 5 |
| SPF | 4.18 | 2.54 | 4.32 | 5.40 | 5.64 |
| Standard deviation (+/−) | 0.30 | 0.27 | 0.22 | 0.68 | 0.64 |

In comparison to example number 1 which contains castor oil, example numbers 4 and 5 show a significant increase in the SPF of the nanotitanium oxides. Additionally, example numbers 3, 4, and 5 show a significant increase in the SPF of the nanotitanium oxides when compared to example number 2, which contains 2-octododecylneopentate.

EXAMPLES 6 TO 9

Influence of the Esters According to the Invention on the SPF in the Presence of Nanozinc Oxide The inventors compared the influence of the esters containing an aromatic group according to the invention on the SPF, with castor oil and 2-octyldodecyl neopentanoate, the photoprotective agent being a nanozinc oxide.

Compositions 6, 7, 8 and 9 below are prepared:

| | | Composition (%) | | | |
|---|---|---|---|---|---|
| | Phase | Ex. 6 (comparative) | Ex. 7 (comparative) | Ex. 8 (invention) | Ex. 9 (invention) |
| Castor oil | A | 83 | | | |
| 2-Octyldodecyl neopentanoate | | | 83 | | |
| Glyceryl dibenzoyl ricinoleate | | | | 83 | |
| Glyceryl monodibenzoyl ricinoleate | | | | | 83 |
| Nanotitanium oxide (Z-Cote sold by the company Sunsmart) | B | 5 | 5 | 5 | 5 |
| Octacosanyl stearate | C | 12 | 12 | 12 | 12 |
| | | 100 | 100 | 100 | 100 |

The same procedure as before is used.

The SPF is measured according to the method of the preceding example.

Results

| | Examples | | | |
|---|---|---|---|---|
| | No. 6 | No. 7 | No. 8 | No. 9 |
| SPF | 2.82 | 2.06 | 2.80 | 2.94 |
| Standard deviation (+/−) | 0.13 | 0.13 | 0.10 | 0.08 |

The results show that example numbers 8 and 9 allow an increase in the SPF of compositions containing a nanozinc oxide in comparison with comparative example number 7 containing 2-octododecylneopentate. Example numbers 8 and 9 show an SPF that is more or less equivalent to that of example number 6.

EXAMPLES 10 TO 13

Influence of the Esters According to the Invention on the SPF in the Presence of a Liposoluble Organic Screening Agent The inventors compared the influence of the esters containing an aromatic group according to the invention on the SPF with 2-octyldodecyl neopentanoate, the photoprotective agent being octyl methoxycinnamate.

Compositions 10, 11, 12 and 13 below are prepared:

| | | Composition (%) | | | |
|---|---|---|---|---|---|
| | Phase | Ex. 10 (comparative) | Ex. 11 (invention) | Ex. 12 (invention) | Ex. 13 (invention) |
| 2-Octyldodecyl neopentanoate | | 85 | | | |
| Glyceryl monobenzoyl ricinoleate | A | | 85 | | |
| Glyceryl dibenzoyl ricinoleate | | | | 85 | |
| Glyceryl monodibenzoyl ricinoleate | | | | | 85 |
| Octyl methoxycinnamate | B | 5 | 5 | 5 | 5 |
| Octacosanyl stearate | C | 10 | 10 | 10 | 10 |
| | | 100 | 100 | 100 | 100 |

Procedure

The constituents of phases A and B are mixed together and homogenized with stirring, at room temperature.

The wax (phase C) is added and the mixture is homogenized at 100° C. by stirring with a magnetic bar.

The mixture is cast at 100° C. in a mould at 40–42° C.

Measurement of the SPF in vitro

For each of the Examples 8 to 10 the sun protection factor (SPF) was determined according to the "in vitro" method described by B. L. Diffey in J. Soc. Cosmet. Chem. 40, 127–133, (1989).

The measurements were performed using a UV-visible SPF 290S spectrophotometer from Optometrics equipped with an integration sphere and a xenon lamp.

Each composition is applied to a Transpore adhesive tape from 3M, stuck to a quartz slide, in the form of a homogeneous and uniform deposit in a proportion of 1.5 mg/cm$^2$.

Results

| | Examples | | | |
|---|---|---|---|---|
| | No. 10 | No. 11 | No. 12 | No. 13 |
| SPF | 6.02 | 8.08 | 7.14 | 6.46 |
| Standard deviation (+/−) | 0.63 | 1.15 | 0.52 | 0.78 |

These results show that the esters of example number 11 allow an increase in the SPF of inorganic screening agents such as octyl methoxycinnamate when compared with a standard oil such as octyldodecyl neopentanoate, as contained in example number 10.

EXAMPLE 14

Care Base for the Lips

| | |
|---|---|
| Glyceryl monodibenzoyl ricinoleate (Finsolv BCO-115) | 22.58% |
| C12–15 Alkylbenzoate | 20.78% |
| Phenyltrimethicone | 5.19% |
| Diisostearyl malate | 7.27% |
| Tridecyl trimellitate | 15.58% |
| Lanolin oil | 13.50% |
| BHT | 0.10% |
| Polyethylene wax (MW = 500) | 3.22% |
| Candelilla wax | 5.64% |
| Carnauba wax | 3.14% |
| Nanotitanium oxide (UV-Titan M 262 from Kemira) | 3.00% |
| | 100.00% |

Procedure

The nanotitanium oxide is ground in the glyceryl monodibenzoyl ricinoleate using a three-roll mill.

The other constituents are then added and the mixture is heated at 100° C. with magnetic stirring until the waxes have melted and the mixture is homogeneous.

The mixture is then cast at 100° C. into the cells of a mould so as to obtain a stick.

EXAMPLE 15

Lipstick

| | |
|---|---|
| Glyceryl monodibenzoyl ricinoleate (Finsolv BCO-115) | 15.58% |
| C12–15 Alkylbenzoate | 20.78% |
| Phenyltrimethicone | 5.19% |
| Diisostearyl malate | 7.27% |
| Tridecyl trimellitate | 15.58% |
| Lanolin oil | 13.50% |
| BHT | 0.10% |
| Polyethylene wax (MW = 500) | 3.22% |
| Candelilla wax | 5.64% |
| Carnauba wax | 3.14% |
| Nanotitanium oxide (UV-Titan M 262 from Kemira) | 3.00% |
| FD & C Yellow 6 Al lake | 3.37% |
| Black iron oxide | 0.06% |
| DC Red 21 Al lake | 0.61% |
| DC Red 7 | 2.96% |
| | 100.00% |

Procedure

The nanotitanium oxide is ground in the glyceryl monodibenzoyl ricinoleate using a three-roll mill.

The pigments are ground in a mixture consisting of the rest of the oily phase, the lanolin and the BHT, in a three-roll mill.

The two ground materials are combined, the waxes are then added and the mixture is heated at 100° C. with magnetic stirring until the waxes have melted and the mixture is homogeneous.

The composition is then cast at 100° C. into the cells of a mould so as to obtain a stick.

What is claimed is:

1. A cosmetic care or makeup composition for a keratin material, in a physiologically acceptable medium, comprising:
    at least one photoprotective agent capable of screening out UV radiation;
    a particulate phase; and
    at least one ester comprising an aromatic group, said at least one ester being liquid at room temperature and resulting from esterification of an aromatic acid with at least one hydroxyl group chosen from pendent hydroxyl groups and terminal hydroxyl groups of hydroxylated aliphatic compounds, said hydroxylated aliphatic compounds being chosen from hydroxylated aliphatic acids and esters thereof.

2. A cosmetic care or makeup composition for a keratin material, in a physiologically acceptable medium, comprising:
    at least one photoprotective agent capable of screening out UV radiation comprising at least one inorganic particulate screening agent; and
    at least one ester comprising an aromatic group, said at least one ester being liquid at room temperature and resulting from esterification of an aromatic acid with at least one hydroxyl group chosen from pendent hydroxyl groups and terminal hydroxyl groups of hydroxylated aliphatic compounds, said hydroxylated aliphatic compounds being chosen from hydroxylated aliphatic acids and esters thereof.

3. The composition of claim 1, wherein the at least one photoprotective agent ranges from 0.1% to 45% of the total weight of the composition.

4. The composition of claim 3, wherein the at least one photoprotective agent ranges from 0.5% to 25% of the total weight of the composition.

5. The composition of claim 2, wherein the at least one photoprotective agent ranges from 0.1% to 45% of the total weight of the composition.

6. The composition of claim 5, wherein the at least one photoprotective agent ranges from 0.5% to 25% of the total weight of the composition.

7. The composition of claim 2, wherein the at least one inorganic particulate screening agent is chosen from treated and untreated metal oxide pigments and nanopigments, said at least one inorganic particulate screening agent being capable of physically blocking out UV radiation by scattering and/or reflection.

8. The composition of claim 2, wherein the at least one inorganic particulate screening agent is chosen from treated and untreated nanopigments-chosen from titanium oxide, zinc oxide, iron oxide, zirconium oxide, and cerium oxide.

9. The composition of claim 8, wherein the nanopigments are chosen from nanotitanium oxides and nanozinc oxides.

10. The composition of claim 8, wherein the nanopigments range from 5 to 500 nm in size.

11. The composition of claim 10, wherein the nanopigments range from 10 to 250 nm in size.

12. The composition of claim 11, wherein the nanopigments range from 10 to 100 nm in size.

13. The composition of claim 8, wherein the nanopigments range from 0.1% to 30% of the total weight of the composition.

14. The composition of claim 13, wherein the nanopigments range from 0.5% to 15% of the total weight of the composition.

15. The composition of claim 1, wherein the aromatic acid is chosen from benzoic acid, phenylacetic acid, cinnamic acid, 3-phenylpropanoic acid, salicylic acid, terephthalic acid, trimellitic acid, pyromellitic acid, and mixtures thereof.

16. The composition of claim 2, wherein the aromatic acid is chosen from benzoic acid, phenylacetic acid, cinnamic acid, 3-phenylpropanoic acid, salicylic acid, terephthalic acid, trimellitic acid, pyromellitic acid, and mixtures thereof.

17. The composition of claim 1, wherein the aromatic acid is benzoic acid.

18. The composition of claim 2, wherein the aromatic acid is benzoic acid.

19. The composition of claim 1, wherein the hydroxylated aliphatic acids comprise from 2 to 40 carbon atoms.

20. The composition of claim 19, wherein the hydroxylated aliphatic acids comprise from 10 to 34 carbon atoms.

21. The composition of claim 20, wherein the hydroxylated aliphatic acids comprise from 12 to 28 carbon atoms.

22. The composition of claim 2, wherein the hydroxylated aliphatic acids comprise from 2 to 40 carbon atoms.

23. The composition of claim 22, wherein the hydroxylated aliphatic acids comprise from 10 to 34 carbon atoms.

24. The composition of claim 23, wherein the hydroxylated aliphatic acids comprise from 12 to 28 carbon atoms.

25. The composition of claim 1, wherein the hydroxylated aliphatic acids comprise from 1 to 20 hydroxyl groups, wherein at least one of said hydroxyl groups is esterified with the aromatic acid.

26. The composition of claim 25, wherein the hydroxylated aliphatic acids comprise from 1 to 10 hydroxyl groups, wherein at least one of said hydroxyl groups is esterified with the aromatic acid.

27. The composition of claim 26, wherein the hydroxylated aliphatic acids comprise from 1 to 6 hydroxyl groups, wherein at least one of said hydroxyl groups is esterified with the aromatic acid.

28. The composition of claim 2, wherein the hydroxylated aliphatic acids comprise from 1 to 20 hydroxyl groups, wherein at least one of said hydroxyl groups is esterified with the aromatic acid.

29. The composition of claim 28, wherein the hydroxylated aliphatic acids comprise from 1 to 10 hydroxyl groups, wherein at least one of said hydroxyl groups is esterified with the aromatic acid.

30. The composition of claim 29, wherein the hydroxylated aliphatic acids comprise from 1 to 6 hydroxyl groups, wherein at least one of said hydroxyl groups is esterified with the aromatic acid.

31. The composition of claim 1, wherein the hydroxylated aliphatic compounds are chosen from:
i) saturated linear monohydroxylated aliphatic monoacids chosen from those of formulae:

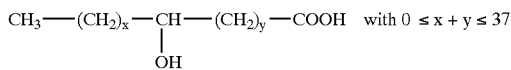

(1) $CH_3-(CH_2)_x-CH(OH)-(CH_2)_y-COOH$ with $0 \leq x+y \leq 37$ and (2) $HO-CH_2-(CH_2)_x-COOH$ with $0 \leq x \leq 38$;

ii) saturated branched monohydroxylated aliphatic monoacids chosen from those of formula:

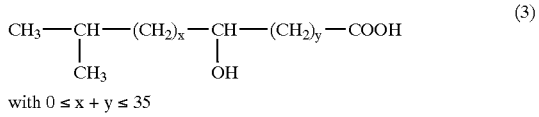

(3) $CH_3-CH(CH_3)-(CH_2)_x-CH(OH)-(CH_2)_y-COOH$ with $0 \leq x+y \leq 35$ and (3') 2-ethyl-3-hydroxycaprylic acid of formula:

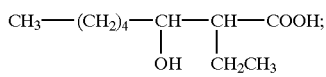

$CH_3-(CH_2)_4-CH(OH)-CH(CH_2CH_3)-COOH$;

iii) unsaturated monohydroxylated aliphatic monoacids chosen from those of formula:

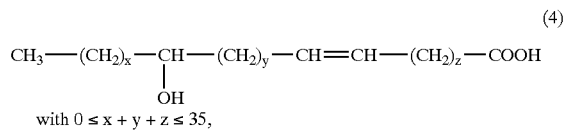

(4) $CH_3-(CH_2)_x-CH(OH)-(CH_2)_y-CH=CH-(CH_2)_z-COOH$ with $0 \leq x+y+z \leq 35$, and

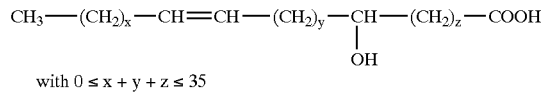

(5) $CH_3-(CH_2)_x-CH=CH-(CH_2)_y-CH(OH)-(CH_2)_z-COOH$ with $0 \leq x+y+z \leq 35$ and (6) $HOCH_2-(CH_2)_x-CH=CH-(CH_2)_y-COOH$ with $0 \leq x+y \leq 36$;

iv) saturated polyhydroxylated aliphatic monoacids of formula:

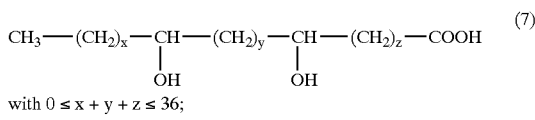

(7) $CH_3-(CH_2)_x-CH(OH)-(CH_2)_y-CH(OH)-(CH_2)_z-COOH$ with $0 \leq x+y+z \leq 36$;

v) saturated monohydroxylated aliphatic polyacids of formula:

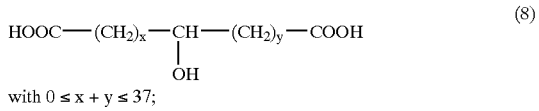

(8) $HOOC-(CH_2)_x-CH(OH)-(CH_2)_y-COOH$ with $0 \leq x+y \leq 37$;

vi) saturated polyhydroxylated aliphatic polyacids;
vii) saturated linear monohydroxylated aliphatic monoacid esters;
viii) unsaturated monohydroxylated aliphatic monoacid esters;
ix) saturated monohydroxylated aliphatic polyacid esters;
x) saturated polyhydroxylated aliphatic polyacid esters;
xi) partial and total esters of a $C_2$ to $C_{16}$ polyol that is reacted with a hydroxylated aliphatic acid;

and mixtures thereof.

32. The composition of claim 31, wherein the saturated linear monohydroxylated aliphatic monoacid esters are chosen from lactic acid esters and 12-hydroxyoctadecanoic acid esters.

33. The composition of claim 31, wherein the unsaturated monohydroxylated aliphatic monoacid esters are chosen from ricinoleic acid esters.

34. The composition of claim 2, wherein the hydroxylated aliphatic compound is chosen from:

i) saturated linear monohydroxylated aliphatic monoacids chosen from those of formula:

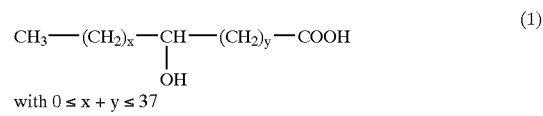

(1) $CH_3-(CH_2)_x-CH(OH)-(CH_2)_y-COOH$ with $0 \leq x+y \leq 37$ and (2) $HO-CH_2-(CH_2)_x-COOH$ with $0 \leq x \leq 38$;

ii) saturated branched monohydroxylated aliphatic monoacids chosen from those of formula:

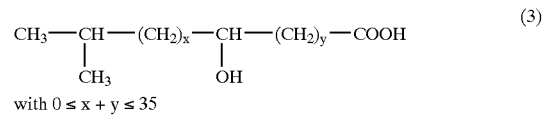

(3) $CH_3-CH(CH_3)-(CH_2)_x-CH(OH)-(CH_2)_y-COOH$ with $0 \leq x+y \leq 35$ and (3') 2-ethyl-3-hydroxycaprylic acid of formula:

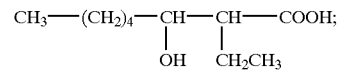

$CH_3-(CH_2)_4-CH(OH)-CH(CH_2CH_3)-COOH$;

iii) unsaturated monohydroxylated aliphatic monoacids chosen from those of formula:

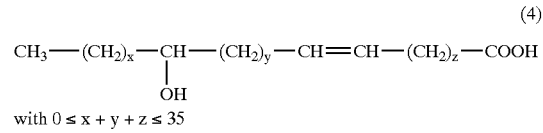

(4) $CH_3-(CH_2)_x-CH(OH)-(CH_2)_y-CH=CH-(CH_2)_z-COOH$ with $0 \leq x+y+z \leq 35$ and

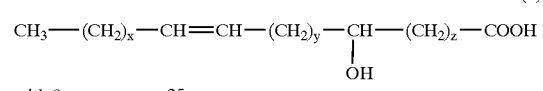

(5) $CH_3-(CH_2)_x-CH=CH-(CH_2)_y-CH(OH)-(CH_2)_z-COOH$ with $0 \leq x+y+z \leq 35$ and (6) $HOCH_2-(CH_2)_x-CH=CH-(CH_2)_y-COOH$ with $0 \leq x+y \leq 36$;

iv) saturated polyhydroxylated aliphatic monoacids of formula:

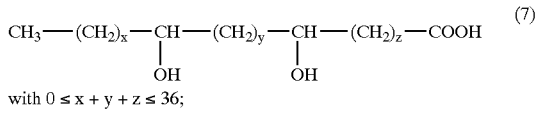

with $0 \leq x + y + z \leq 36$;

v) saturated monohydroxylated aliphatic polyacids of formula:

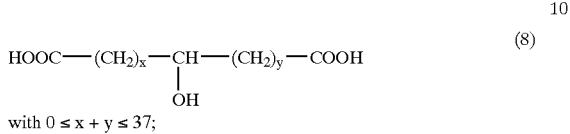

with $0 \leq x + y \leq 37$;

vi) saturated polyhydroxylated aliphatic polyacids;
vii) saturated linear monohydroxylated aliphatic monoacid esters;
viii) unsaturated monohydroxylated aliphatic monoacid esters;
ix) saturated monohydroxylated aliphatic polyacid esters;
x) saturated polyhydroxylated aliphatic polyacid esters;
xi) partial and total esters of a $C_2$ to $C_{16}$ polyol that is reacted with a hydroxylated aliphatic acid;
and mixtures thereof.

35. The composition of claim 34, wherein the saturated linear monohydroxylated aliphatic monoacid esters are chosen from lactic acid esters and 12-hydroxyoctadecanoic acid esters.

36. The composition of claim 34, wherein the unsaturated monohydroxylated aliphatic monoacid esters are chosen from ricinoleic acid esters.

37. The composition of claim 1, wherein the hydroxylated aliphatic compounds are chosen from:

lactic acid; 12-hydroxyoctadecanoic acid; α-hydroxyoctadecanoic acid;

glycolic acid and juniperic acid;

leucinic acid and 2-ethyl-3-hydroxycaprylic acid;

ricinoleic acid;

3-hydroxy-4-hexanoic acid and oxynervonic acid;

16-hydroxy-6-hexadecenoic acid;

9,10-dihydroxyoctadecanoic acid, 9,12-dihydroxyoctadecanoic acid, aleuritic acid, 9,10,12-trihydroxyoctadecanoic acid, hexahydroxyoctadecanoic acid, and octahydroxyoctadecanoic acid;

malic acid and citric acid;

tartaric acid;

isostearyl lactate that is derived from a $C_{12}$–$C_{13}$ alcohol, octyldodecyl lactate, oleyl lactate, and myristyl lactate;

2-ethylhexyl hydroxystearate, octyldodecyl hydroxystearate, isostearyl hydroxystearate, isodecyl hydroxystearate, glyceryl trihydroxystearate, and dipentaerythrityl hexahydroxystearate;

butyl ricinoleate, octyldodecyl ricinoleate, cetyl ricinoleate, glyceryl triricinoleate, and castor oil;

diisostearyl malate, triisostearyl citrate, and trioctyldodecyl citrate;

tartrate that is derived from branched $C_{12}$–$C_{13}$ dialcohols;
and mixtures thereof.

38. The composition of claim 2, wherein the hydroxylated aliphatic compound is chosen from:

lactic acid; 12-hydroxyoctadecanoic acid; α-hydroxyoctadecanoic acid;

glycolic acid and juniperic acid;

leucinic acid and 2-ethyl-3-hydroxycaprylic acid;

ricinoleic acid;

3-hydroxy-4-hexanoic acid and oxynervonic acid;

16-hydroxy-6-hexadecenoic acid;

9,10-dihydroxyoctadecanoic acid, 9,12-dihydroxyoctadecanoic acid, aleuritic acid, 9,10,12-trihydroxyoctadecanoic acid, hexahydroxyoctadecanoic acid, and octahydroxyoctadecanoic acid;

malic acid and citric acid;

tartaric acid;

isostearyl lactate that is derived from a $C_{12}$–$C_{13}$ alcohol, octyldodecyl lactate, oleyl lactate, and myristyl lactate;

2-ethylhexyl hydroxystearate, octyldodecyl hydroxystearate, isostearyl hydroxystearate, isodecyl hydroxystearate, glyceryl trihydroxystearate, and dipentaerythrityl hexahydroxystearate;

butyl ricinoleate, octyldodecyl ricinoleate, cetyl ricinoleate, glyceryl triricinoleate, and castor oil;

diisostearyl malate, triisostearyl citrate, and trioctyldodecyl citrate;

tartrate that is derived from branched $C_{12}$–$C_{13}$ dialcohols;
and mixtures thereof.

39. The composition of claim 1, wherein said at least one ester is chosen from esters of aliphatic fatty acid esters, said aliphatic fatty acid esters comprising a fatty acid residue comprising at least 12 carbon atoms.

40. The composition of claim 2, wherein said at least one ester is chosen from esters of aliphatic fatty acid esters, said aliphatic fatty acid esters comprising a fatty acid residue comprising at least 12 carbon atoms.

41. The composition of claim 1, wherein the hydroxylated aliphatic compounds are chosen from ricinoleic acid esters, 12-hydroxystearic acid esters, lactic acid esters, 14-hydroxyeicosenoic acid esters, and mixtures thereof.

42. The composition of claim 2, wherein the hydroxylated aliphatic compounds are chosen from ricinoleic acid esters, 12-hydroxystearic acid esters, lactic acid esters, 14-hydroxyeicosenoic acid esters, and mixtures thereof.

43. The composition of claim 1, wherein said at least one ester is chosen from glyceryl monobenzoyl ricinoleate, glyceryl mono-dibenzoyl ricinoleate, glyceryl dibenzoyl ricinoleate, glyceryl tribenzoyl ricinoleate, and mixtures thereof.

44. The composition of claim 2, wherein said at least one ester is chosen from glyceryl monobenzoyl ricinoleate, glyceryl mono-dibenzoyl ricinoleate, glyceryl dibenzoyl ricinoleate, glyceryl tribenzoyl ricinoleate, and mixtures thereof.

45. The composition of claim 1, wherein said at least one ester is glyceryl mono-dibenzoyl ricinoleate.

46. The composition of claim 2, wherein said at least one ester is glyceryl mono-dibenzoyl ricinoleate.

47. A cosmetic care or makeup composition for a keratin material, in a physiologically acceptable medium, comprising:

at least one photoprotective agent capable of screening out UV radiation;

a particulate phase; and at least one ester comprising an aromatic group, said at least one ester being liquid at room temperature and chosen from glyceryl monobenzoyl ricinoleate, glyceryl mono-dibenzoyl ricinoleate, glyceryl dibenzoyl ricinoleate, and glyceryl tribenzoyl ricinoleate.

48. The composition of claim 47, wherein said at least one ester is glyceryl mono-dibenzoyl ricinoleate.

49. A cosmetic care or makeup composition for a keratin material, in a physiologically acceptable medium, comprising:
at least one photoprotective agent capable of screening out UV radiation comprising at least one inorganic particulate screening agent; and
at least one ester comprising an aromatic group, said at least one ester being liquid at room temperature and chosen from glyceryl monobenzoyl ricinoleate, glyceryl mono-dibenzoyl ricinoleate, glyceryl dibenzoyl ricinoleate, glyceryl tribenzoyl ricinoleate, and mixtures thereof.

50. The composition of claim 49, wherein said at least one ester is glyceryl mono dibenzoyl ricinoleate.

51. The composition of claim 1, wherein said at least one ester ranges from 0.1% to 99.9% of the total weight of the composition.

52. The composition of claim 51, wherein said at least one ester ranges from 1% to 99% of the total weight of the composition.

53. The composition of claim 52, wherein said at least one ester ranges from 5% to 90% of the total weight of the composition.

54. The composition of claim 2, wherein said at least one ester ranges from 0.1% to 99.9% of the total weight of the composition.

55. The composition of claim 54, wherein said at least one ester ranges from 1% to 99% of the total weight of the composition.

56. The composition of claim 55, wherein said at least one ester ranges from 5% to 90% of the total weight of the composition.

57. The composition of claim 1, wherein said at least one ester is in a ratio to said at least one photoprotective agent of from 999:1 to 0.01:1.

58. The composition of claim 57, wherein said at least one ester is in a ratio to said at least on photoprotective agent of from 200:1 to 1:1.

59. The composition of claim 2, wherein said at least one ester is in a ratio to said at least one photoprotective agent of from 999:1 to 0.01:1.

60. The composition of claim 59, wherein said at least one ester is in a ratio to said at least on photoprotective agent of from 200:1 to 1:1.

61. The composition of claim 1, further comprising at least one ingredient chosen from pigments and nacres.

62. The composition of claim 2, further comprising at least one ingredient chosen from pigments and nacres.

63. The composition of claim 1, further comprising at least one fatty substance chosen from waxes, oils, fatty substances that are pasty at room temperature, gums, resins, and lipophilic polymers.

64. The composition of claim 2, further comprising at least one fatty substance chosen from waxes, oils, fatty substances that are pasty at room temperature, gums, resins, and lipophilic polymers.

65. The composition of claim 1, further comprising at least one wax.

66. The composition of claim 2, further comprising at least one wax.

67. The composition of claim 63, wherein the at least one fatty substance ranges from 0.01% to 90% of the total weight of the composition.

68. The composition of claim 67, wherein the at least one fatty substance ranges from 0.05% to 60% of the total weight of the composition.

69. The composition of claim 68, wherein the at least one fatty substance ranges from 1% to 35% of the total weight of the composition.

70. The composition of claim 64, wherein the at least one fatty substance ranges from 0.01% to 90% of the total weight of the composition.

71. The composition of claim 70, wherein the at least one fatty substance ranges from 0.05% to 60% of the total weight of the composition.

72. The composition of claim 71, wherein the at least one fatty substance ranges from 1% to 35% of the total weight of the composition.

73. The composition of claim 1, further comprising at least one additive chosen from softeners, antioxidants, preserving agents, opacifiers, neutralizers, stabilizers, emollients, silicones, fluoro compounds, antifoams, fragrances, surfactants, polymers, propellants, acidifying agents, basifying agents, lipophilic gelling agents, liquid fatty substances, dispersants, dyestuffs, cosmetic active agents, and dermatological active agents.

74. The composition of claim 2, further comprising at least one additive chosen from softeners, antioxidants, preserving agents, opacifiers, neutralizers, stabilizers, emollients, silicones, fluoro compounds, antifoams, fragrances, surfactants, polymers, propellants, acidifying agents, basifying agents, lipophilic gelling agents, liquid fatty substances, dispersants, dyestuffs, cosmetic active agents, and dermatological active agents.

75. The composition of claim 73, wherein the at least one additive ranges from 0.001% to 30% of the total weight of the composition.

76. The composition of claim 75, wherein the at least one additive ranges from 0.005% to 10% of the total weight of the composition.

77. The composition of claim 74, wherein the at least one additive ranges from 0.001% to 30% of the total weight of the composition.

78. The composition of claim 77, wherein the at least one additive ranges from 0.005% to 10% of the total weight of the composition.

79. The composition of claim 1, wherein said composition is in a form chosen from oily solutions, oily gels, anhydrous gels, oil-in-water emulsions, water-in-oil emulsions, multiple emulsions, and dispersions of oil in water by means of vesicles.

80. The composition of claim 2, wherein said composition is in a form chosen from oily solutions, oily gels, anhydrous gels, oil-in-water emulsions, water-in-oil emulsions, multiple emulsions, and dispersions of oil in water by means of vesicles.

81. The composition of claim 1, wherein said composition is for protecting human epidermis against UV rays, and further wherein said composition is in a form chosen from cast products, soft pastes, creams, milks, ointments, gels, cream gels, sticks, solid tubes, powders, aerosol mousses, and sprays.

82. The composition of claim 1, wherein said composition is an antisun composition, and further wherein said antisun composition is in a form chosen from cast products, soft pastes, creams, milks, ointments, gels, cream gels, sticks, solid tubes, powders, aerosol mousses, and sprays.

83. The composition of claim 2, wherein said composition is for protecting human epidermis against UV rays, and further wherein said composition is in a form chosen from cast products, soft pastes, creams, milks, ointments, gels, cream gels, sticks, solid tubes, powders, aerosol mousses, and sprays.

84. The composition of claim 2, wherein said composition is an antisun composition, and further wherein said antisun composition is in a form chosen from cast products, soft pastes, creams, milks, ointments, gels, cream gels, sticks, solid tubes, powders, aerosol mousses, and sprays.

85. A composition for protecting human epidermis against UV rays or an antisun composition comprising, in a physiologically acceptable medium:
- at least one photoprotective agent capable of screening out UV radiation;
- a particulate phase; and
- at least one ester comprising an aromatic group, said at least one ester being liquid at room temperature and resulting from esterification of an aromatic acid with at least one hydroxyl group chosen from pendent hydroxyl groups and terminal hydroxyl groups of hydroxylated aliphatic compounds, said hydroxylated aliphatic compounds being chosen from hydroxylated aliphatic acids and esters thereof.

86. A composition for protecting human epidermis against UV rays or an antisun composition comprising, in a physiologically acceptable medium:
- at least one photoprotective agent capable of screening out UV radiation comprising at least one inorganic particulate screening agent; and
- at least one ester comprising an aromatic group, said at least one ester being liquid at room temperature and resulting from esterification of an aromatic acid with at least one hydroxyl group chosen from pendent hydroxyl groups and terminal hydroxyl groups of hydroxylated aliphatic compounds, said hydroxylated aliphatic compounds being chosen from hydroxylated aliphatic acids and esters thereof.

87. The composition of claim 1, wherein said composition is for protecting hair against UV rays, and further wherein said composition is in a form chosen from shampoos, conditioners, and lotions.

88. The composition of claim 2, wherein said composition is for protecting hair against UV rays, and further wherein said composition is in a form chosen from shampoos, conditioners, and lotions.

89. A composition for protecting hair against UV rays, comprising, in a physiologically acceptable medium:
- at least one photoprotective agent capable of screening out UV radiation;
- a particulate phase; and
- at least one ester comprising an aromatic group, said at least one ester being liquid at room temperature and resulting from esterification of an aromatic acid with at least one hydroxyl group chosen from pendent hydroxyl groups and terminal hydroxyl groups of hydroxylated aliphatic compounds, said hydroxylated aliphatic compounds being chosen from hydroxylated aliphatic acids and esters thereof.

90. A composition for protecting hair against UV rays, in a physiologically acceptable medium, comprising:
- at least one photoprotective agent capable of screening out UV radiation comprising at least one inorganic particulate screening agent; and
- at least one ester comprising an aromatic group, said at least one ester being liquid at room temperature and resulting from esterification of an aromatic acid with at least one hydroxyl group chosen from pendent hydroxyl groups and terminal hydroxyl groups of hydroxylated aliphatic compounds, said hydroxylated aliphatic compounds being chosen from hydroxylated aliphatic acids and esters thereof.

91. The composition of claim 1, wherein said composition is a makeup composition for eyelashes, eyebrows, skin, or lips.

92. The composition of claim 2, wherein said composition is a makeup composition for eyelashes, eyebrows, skin, or lips.

93. A makeup composition for eyelashes, eyebrows, skin, or lips comprising, in a physiologically acceptable medium:
- at least one photoprotective agent capable of screening out UV radiation;
- a particulate phase; and
- at least one ester comprising an aromatic group, said at least one ester being liquid at room temperature and resulting from esterification of an aromatic acid with at least one hydroxyl groups chosen from pendent hydroxyl groups and terminal hydroxyl groups of hydroxylated aliphatic compounds, said hydroxylated aliphatic compounds being chosen from hydroxylated aliphatic acids and esters thereof.

94. A makeup composition for eyelashes, eyebrows, skin, or lips, in a physiologically acceptable medium, comprising:
- at least one photoprotective agent capable of screening out UV radiation comprising at least one inorganic particulate screening agent; and
- at least one ester comprising an aromatic group, said at least one ester being liquid at room temperature and resulting from esterification of an aromatic acid with at least one hydroxyl group chosen from pendent hydroxyl groups and terminal hydroxyl groups of hydroxylated aliphatic compounds, said hydroxylated aliphatic compounds being chosen from hydroxylated aliphatic acids and esters thereof.

95. The composition of claim 1, wherein said composition is a makeup composition for lips.

96. The composition of claim 2, wherein said composition is a makeup composition for lips.

97. The composition of claim 1, wherein said composition is in anhydrous form.

98. The composition of claim 2, wherein said composition is in anhydrous form.

99. The composition of claim 1, wherein said composition is in solid form at room temperature.

100. The composition of claim 2, wherein said composition is in solid form at room temperature.

101. The composition of claim 1, wherein said composition is in a form for protecting skin, lips, or integuments against UV radiation.

102. The composition of claim 101, wherein said UV radiation is solar radiation.

103. The composition of claim 2, wherein said composition is in a form for protecting skin, lips, or integuments against UV radiation.

104. The composition of claim 103, wherein said UV radiation is solar radiation.

105. A method of making a composition of improved photoprotective power for protection of skin, lips, or integuments against UV radiation comprising:
- combining an effective amount of (i) at least one photoprotective agent and (ii) at least one ester comprising an aromatic group, said at least one ester being liquid at room temperature and resulting from esterification of an aromatic acid with at least one hydroxyl group chosen from pendent hydroxyl groups and terminal hydroxyl groups of hydroxylated aliphatic compounds, said hydroxylated aliphatic compounds being chosen from hydroxylated aliphatic acids and esters thereof, wherein said composition is in a physiologically acceptable medium.

106. A method of making an antisun composition comprising:
combining (i) at least one photoprotective agent with (ii) at least one ester comprising an aromatic group, said at least one ester being liquid at room temperature and resulting from esterification of an aromatic acid with at least one hydroxyl group chosen from pendent hydroxyl groups and terminal hydroxyl groups of hydroxylated aliphatic compounds, said hydroxylated aliphatic compounds being chosen from hydroxylated aliphatic acids and esters thereof, wherein said composition is in a physiologically acceptable medium.

107. The method of claim 105, wherein the at least one photoprotective agent ranges from 0.1% to 45% of the total weight of the composition.

108. The method of claim 107, wherein the at least one photoprotective agent ranges from 0.5% to 25% of the total weight of the composition.

109. The method of claim 106, wherein the at least one photoprotective agent ranges from 0.1% to 45% of the total weight of the composition.

110. The method of claim 109, wherein the at least one photoprotective agent ranges from 0.5% to 25% of the total weight of the composition.

111. The method of claim 105, wherein the at least one photoprotective agent is chosen from UV-active hydrophilic organic screening agents, lipophilic organic screening agents, and inorganic screening agents.

112. The method of claim 106, wherein the at least one photoprotective agent is chosen from UV-active hydrophilic organic screening agents, lipophilic organic screening agents, and inorganic screening agents.

113. The method of claim 111, wherein the UV-active hydrophilic organic screening agents and the lipophilic organic screening agents are chosen from cinnamic derivatives, dibenzoylmethane derivatives, salicylic derivatives, camphor derivatives, triazine derivatives, benzophenone derivatives, β,β'-diphenylacrylate derivatives, benzimidazole derivatives, bis-benzazolyl derivatives, bis-hydroxyphenolbenzotriazole derivatives, p-aminobenzoic acid derivatives, screening hydrocarbon-based polymers, screening silicones, and mixtures thereof.

114. The method of claim 112, wherein the UV-active hydrophilic organic screening agents or the lipophilic organic screening agents are chosen from cinnamic derivatives, dibenzoylmethane derivatives, salicylic derivatives, camphor derivatives, triazine derivatives, benzophenone derivatives, β,β'-diphenylacrylate derivatives, benzimidazole derivatives, bis-benzazolyl derivatives, bis-hydroxyphenolbenzotriazole derivatives, p-aminobenzoic acid derivatives, screening hydrocarbon-based polymers, screening silicones, and mixtures thereof.

115. The method of claim 105, wherein the at least one photoprotective agent comprises at least one inorganic particulate screening agent chosen from treated and untreated metal oxide pigments and nanopigments, said at least one inorganic particulate screening agent being capable of physically blocking out UV radiation by scattering and/or reflection.

116. The method of claim 106, wherein the at least one photoprotective agent comprises at least one inorganic particulate screening agent chosen from treated and untreated metal oxide pigments and nanopigments, said at least one inorganic particulate screening agent being capable of physically blocking out UV radiation by scattering and/or reflection.

117. The method of claim 105, wherein the at least one photoprotective agent comprises at least one inorganic particulate screening agent chosen from treated and untreated metal oxide pigments and nanopigments, said at least one inorganic particulate screening agent being capable of physically blocking out UV radiation by scattering and/or reflection.

118. The method of claim 106, wherein the at least one photoprotective agent comprises at least one inorganic particulate screening agent chosen from treated and untreated metal oxide pigments and nanopigments, said at least one inorganic particulate screening agent being capable of physically blocking out UV radiation by scattering and/or reflection.

119. The method of claim 117, wherein the at least one inorganic particulate screening agent is chosen from treated and untreated nanopigments chosen from titanium oxide, zinc oxide, iron oxide, zirconium oxide, and cerium oxide.

120. The method of claim 118, wherein the at least one inorganic particulate screening agent is chosen from treated and untreated nanopigments chosen from titanium oxide, zinc oxide, iron oxide, zirconium oxide, and cerium oxide.

121. The method of claim 119, wherein the nanopigments are chosen from nanotitanium oxides and nanozinc oxides.

122. The method of claim 120, wherein the nanopigments are chosen from nanotitanium oxides and nanozinc oxides.

123. The method of claim 119, wherein the nanopigments range from 5 to 500 nm in size.

124. The method of claim 123, wherein the nanopigments range from 10 to 250 nm in size.

125. The method of claim 124, wherein the nanopigments range from 10 to 100 nm in size.

126. The method of claim 120, wherein the nanopigments range from 5 to 500 nm in size.

127. The method of claim 126, wherein the nanopigments range from 10 to 250 nm in size.

128. The method of claim 127, wherein the nanopigments range from 10 to 100 nm in size.

129. The method of claim 105, wherein said at least one ester is in a ratio to said at least one photoprotective agent of from 999:1 to 0.01:1.

130. The method of claim 129, wherein said ratio is from 200:1 to 1:1.

131. The method of claim 106, wherein said at least one ester is in a ratio to said at least one photoprotective agent of from 999:1 to 0.01:1.

132. The method of claim 131, wherein said ratio is from 200:1 to 1:1.

133. A method of protecting human skin, lips, or integuments against solar radiation comprising:
including in a cosmetic composition comprising a physiologically acceptable medium (i) at least one photoprotective agent and (ii) an effective amount of at least one ester comprising an aromatic group, said at least one ester being liquid at room temperature and resulting from esterification of an aromatic acid with at least one hydroxyl group chosen from pendent hydroxyl groups and terminal hydroxyl groups of hydroxylated aliphatic compounds, said hydroxylated aliphatic compounds being chosen from hydroxylated aliphatic acids and esters thereof.

134. A method for increasing an antisun protective property of a cosmetic composition comprising:
including in a cosmetic composition comprising a physiologically acceptable medium (i) at least one photoprotective agent and (ii) an effective amount of at least one ester comprising an aromatic group, said at least one ester being liquid at room temperature and resulting from esterification of an aromatic acid with at least one hydroxyl group chosen from pendent hydroxyl groups and terminal hydroxyl groups of hydroxylated aliphatic compounds, said hydroxylated aliphatic compounds being chosen from hydroxylated aliphatic acids and esters thereof.

135. A method for increasing sun protection factor of a cosmetic composition comprising:

including in a cosmetic composition comprising a physiologically acceptable medium (i) at least one photo-protective agent and (ii) an effective amount of at least one ester comprising an aromatic group, said at least one ester being liquid at room temperature and resulting from esterification of an aromatic acid with at least one hydroxyl group chosen from pendent hydroxyl groups and terminal hydroxyl groups of hydroxylated aliphatic compounds, said hydroxylated aliphatic compounds being chosen from hydroxylated aliphatic acids and esters thereof.

* * * * *

UNITED STATES PATENT AND TRADEMARK OFFICE
CERTIFICATE OF CORRECTION

PATENT NO. : 6,869,597 B2
DATED : March 22, 2005
INVENTOR(S) : Pascal Arnaud

It is certified that error appears in the above-identified patent and that said Letters Patent is hereby corrected as shown below:

<u>Title page,</u>
Item [57] ABSTRACT,
Line 7, "pendent hydroxyl group and" should read -- pendent hydroxyl groups and --.
Line 8-9, "compounds said" should read -- compounds, said --.

<u>Column 19,</u>
Line 62, "nanopigments-chosen" should read -- nanopigments chosen --.

<u>Column 25,</u>
Line 15, "mono dibenzoyl" should read -- mono-dibenzoyl --.
Lines 38 and 44, "on" should read -- one --.

<u>Column 28,</u>
Line 18, "groups chosen" should read -- group chosen --.

Signed and Sealed this

Seventh Day of June, 2005

JON W. DUDAS
*Director of the United States Patent and Trademark Office*